United States Patent

Schnepp-Pesch et al.

[11] Patent Number: 5,860,999
[45] Date of Patent: Jan. 19, 1999

[54] STENT AND METHOD OF USING SAME

[75] Inventors: Wolfram Schnepp-Pesch; Josef Lindenberg, both of Karlsruhe, Germany

[73] Assignee: Angiomed GmbH & Co.Medizintechnik KG, Karlsruhe, Germany

[21] Appl. No.: 978,056

[22] Filed: Nov. 25, 1997

Related U.S. Application Data

[63] Continuation of Ser. No. 495,625, filed as PCT/EP94/00168 Jan. 22, 1994, Pat. No. 5,707,386.

[30]    Foreign Application Priority Data

Feb. 4, 1993 [DE] Germany ............... 43 03 181.1

[51] Int. Cl.$^6$ ............................................. A61M 29/00
[52] U.S. Cl. ............................... 606/194; 606/191; 623/1; 623/12
[58] Field of Search ................... 606/191, 198, 606/192, 195, 194; 623/1, 12

[56]         References Cited

U.S. PATENT DOCUMENTS

| | | |
|---|---|---|
| 5,104,404 | 4/1992 | Wolff . |
| 5,135,536 | 8/1992 | Hillstead . |
| 5,158,548 | 10/1992 | Lau et al. ................... 604/96 |
| 5,195,984 | 3/1993 | Schatz ....................... 606/195 |
| 5,421,955 | 6/1995 | Lau et al. ................... 606/198 |
| 5,514,154 | 5/1996 | Lau et al. ................... 606/195 |
| 5,591,197 | 1/1997 | Orth et al. .................. 606/191 |
| 5,697,971 | 12/1997 | Fischell et al. ............. 606/195 |

FOREIGN PATENT DOCUMENTS

| | | |
|---|---|---|
| 0540290A3 | 5/1993 | European Pat. Off. . |
| 1766921 | 1/1970 | Germany . |

*Primary Examiner*—Michael Buiz
*Assistant Examiner*—Kevin Truong
*Attorney, Agent, or Firm*—Antonelli, Terry, Stout & Kraus, LLP

[57]            ABSTRACT

A stent, which has an easier and better bendability and higher flexibility than known stents, has several meander paths (2,2a,2b,2c) successively arranged in the axial direction (A) and extending over its circumference (U), and between axially facing areas (3,3a,3'a,3b), interconnected by connecting areas (4,4a,4b,4c), of the meander paths (2,2a,2b,2c) in the circumferential direction (U) there are at least two facing, non-interconnected areas (3,3a,3'a,3b) of each meander path (2,2a,2b,2c)

13 Claims, 3 Drawing Sheets

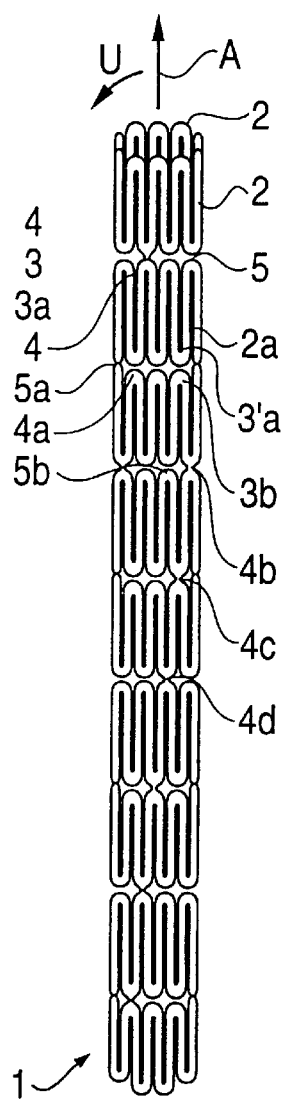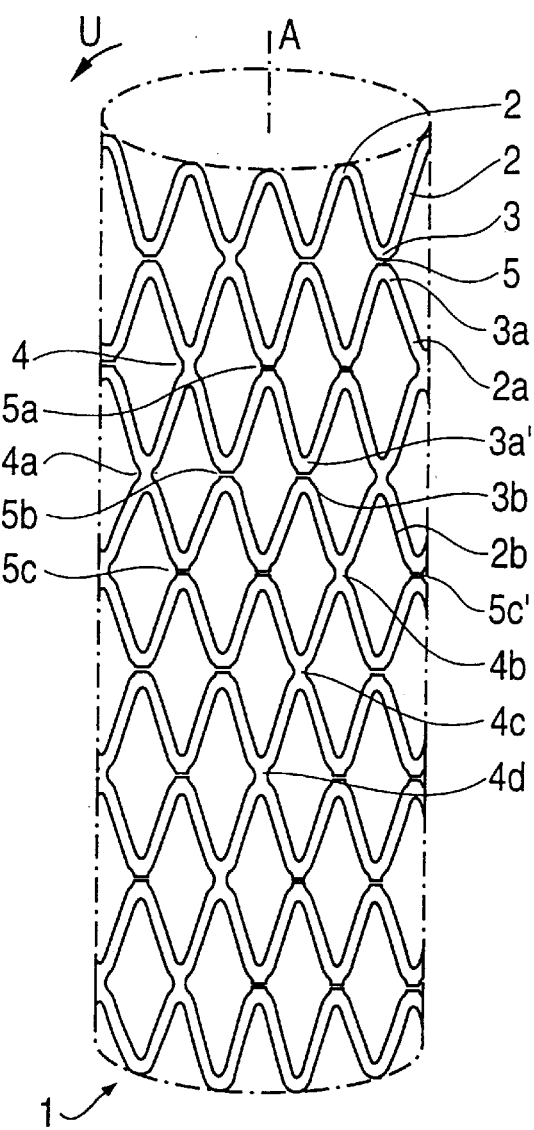

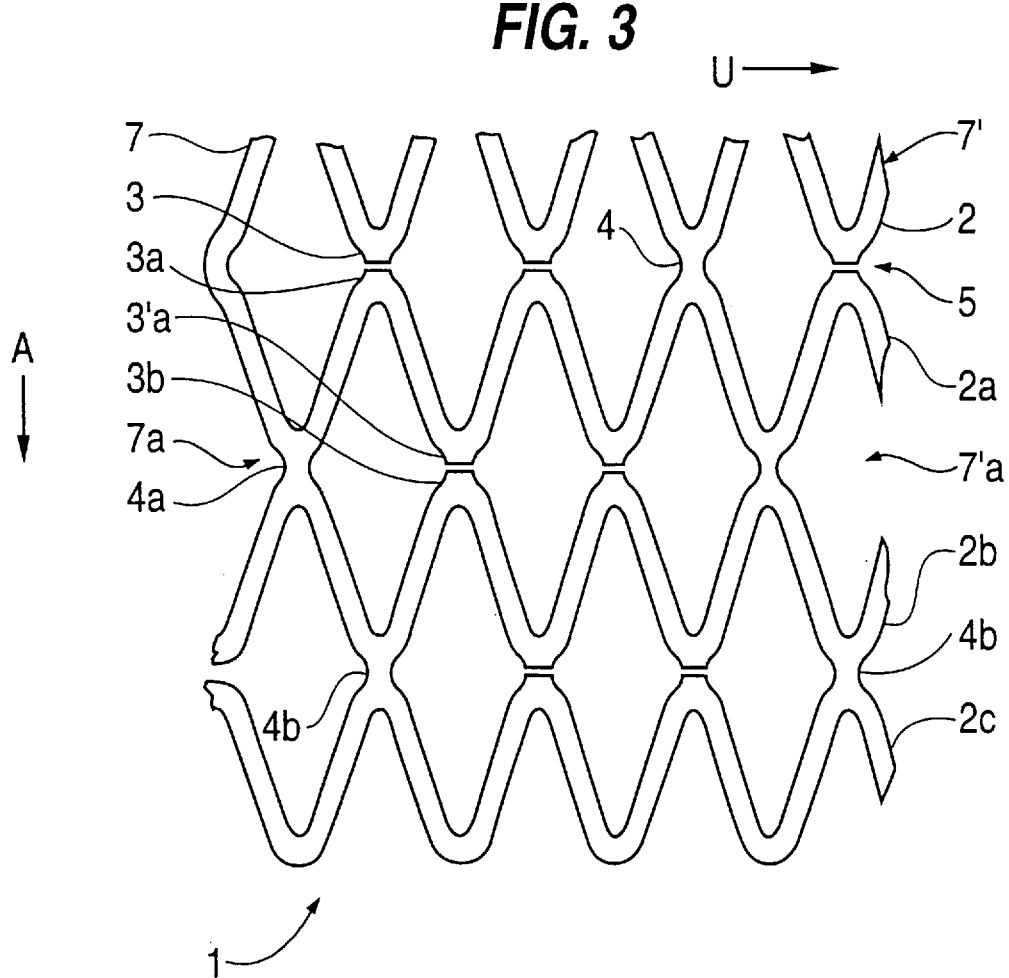

5,860,999

STENT AND METHOD OF USING SAME

This application is a Continuation of application Ser. No. 08/495,625, filed Sep. 21, 1995 now U.S. Pat. No. 5,707, 386, the specification of which was filed as PCT International Application No. PCT/EP94/00168 filed Jan. 22, 1994.

FIELD OF THE INVENTION

The invention relates to a stent.

BACKGROUND OF THE INVENTION

Such stents or implantable catheters, which can be inserted in a body cavity, a vessel or the like, can be made from plastic or an inert metal, such as steel or nickel-titanium alloys. Such stents are in particular known as endovascular or endoluminal stents or intraluminal tubes. The stents are e.g. used for widening the ureter in the prostate region in the case of benign prostate hyperplasia (BPH) or in the case of sclerotic blood vessels for widening and keeping open the same. The stents have material areas and gaps between them. Thus, the parietal tissue of the organ kept open can grow round the stent. Stents can have a spiral construction or can be in the form of a helically wound coil. They can also be made from woven, knitted or braided wire or plastic material. Such stents can have memory characteristics, such as e.g. occur with certain nickel-titanium alloys (nitinol).

A problem with such stents is their limited bendability, particularly on introducing through narrow organs, such as blood vessels, at the point where a widening can take place. There is a risk that on bending the stent bends in in the center as a result of the action of axially vertically directed forces, in that its cross-sectional area is reduced in the direction of the acting forces, but is widened perpendicular thereto and to the axial direction thereof. This can make insertion more difficult and can also damage the surrounding tissue, particularly if the stent is to be inserted in a bend area of the vessel or the like. Stents are relatively stiff and inflexible. This more particularly applies with stents having a rhombic structure, which are e.g. produced by cutting from nickel-titanium sheeting and have memory characteristics.

SUMMARY OF THE INVENTION

The problem of the invention is consequently to provide a stent, which as a high bending flexibility in the case of axially vertically acting forces and which is in particular subject to no deformations of its contour, particularly suffering no cross-sectional changes in the case of bending.

According to the invention this problem is solved by a stent, which is characterized in that it has several axially succeeding meander paths extending over its circumference, that between axially facing areas of the meander paths interconnected by connecting portions in the circumferential direction there are at least two facing, non-interconnected areas of each meander path.

Due to the fact that with such a stent and with several axially succeeding material paths guided in meander-like manner over the circumference facing or directed towards one another, adjacent areas of two adjacent meander paths are not interconnected in all cases, but instead between such interconnected areas there are circumferentially at least two non-interconnected areas, a higher flexibility is obtained than would be the case with a stent in which all the facing, adjacent areas of two adjacent meander paths were firmly interconnected. This not only leads to a higher flexibility, but it is in particular achieved that no cross-sectional deformation occurs at bends under the action of axially vertical forces.

An important advantage of the invention is that a high bendability is achieved without multilayer material crossing points, such as is the case in knitted, woven and braided structures. Due to the fact that there are no such material crossing points, the stent according to the invention grows better into the tissue. It also significantly reduces or eliminates the risk of the occurrence of thromboses, particularly in the vascular region.

According to a preferred development the connecting portions of axially succeeding meander paths are reciprocately displaced in the circumferential direction and in particular the connecting portions are circumferentially displaced by half a meander period, so that the desired axial strength is retained or obtained.

The meander paths can be formed in numerous different ways. Thus, according to preferred developments, the meander paths are zig-zag-like (with peaks), the meander paths are sinusoidal and that the meander paths have an oval construction. According to further preferred developments facing areas of the meander paths are aligned in the axial direction and/or that the width of the connecting areas in the circumferential direction is no larger than the width of the legs of the meander paths.

The stent is preferably self-expanding and is made from a memory metal material. In the low temperature state (well below body temperature), the individual meander legs engage with one another, whereas in the high temperature state (below but closer to body temperature) the stent is radially widened.

Further advantages and features of the invention can be gathered from the claims and the following description of the inventive stent with reference to the attached drawings.

BRIEF DESCRIPTION OF DRAWINGS

FIG. 1 is a preferred development of the stent according to the invention in its low temperature or insertion configuration.

FIG. 2 is the stent of FIG. 1 in its high temperature of positioning configuration.

FIG. 3 is a diagrammatic representation of a stent separated longitudinally at its welding positions and laid out flat in order to better illustrate the connection of the successive, axial, zig-zag meander paths.

DETAILED DESCRIPTION OF DISCLOSED EMBODIMENT

Figure 4:
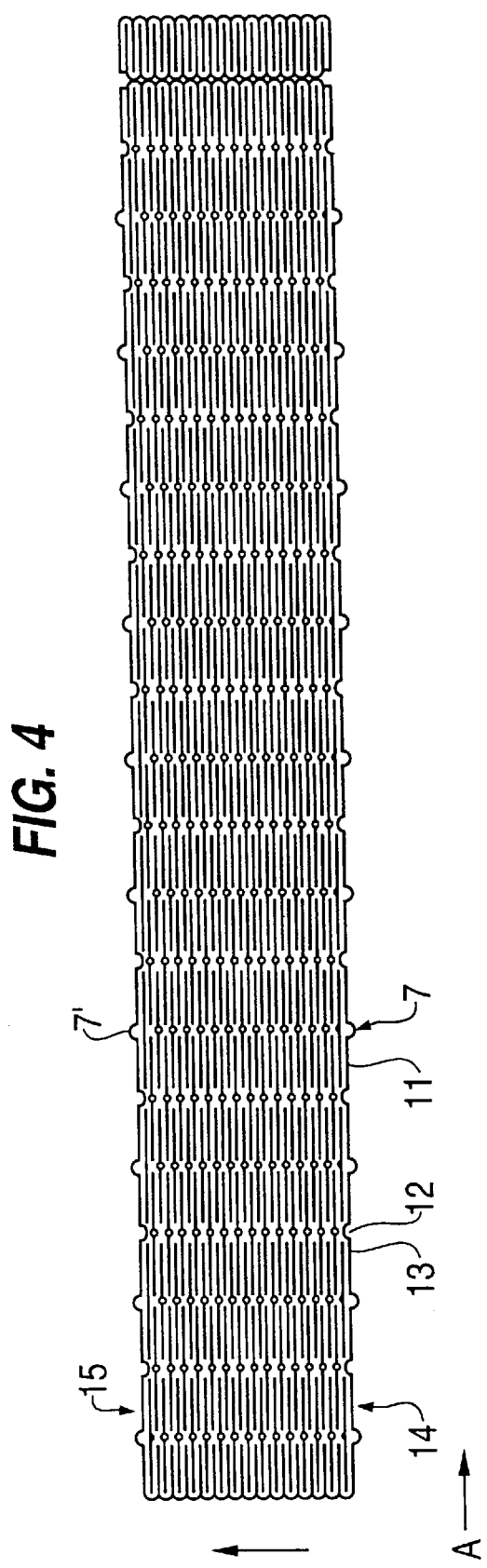
FIG. 4 is a slotted plate for producing a stent according to the invention.

In the represented embodiment the stent 1 according to the invention has a cylindrical shape, the outer contour of the stent being indicated by broken lines S in FIG. 2.

In place of a cylindrical design the stent 1 can also have a conical, biconical, frustum-shaped or other contour. It always has an axis of symmetry A, which determines the axial direction. The circumferential direction is indicated by the arrow U.

As can in particular be gathered from FIGS. 2 and 3, the stent 1 according to the invention comprises a number of meander paths 2, 2a, 2b succeeding one another in the axial direction A. In the circumferential direction the meander paths 2, 2a, 2b are arranged in such a way that in each case facing, adjacent peak areas 3, 3*a* or 3'*a*, 3*b* of in each case juxtaposed meander paths 2, 2*a*, 2*b* are axially aligned.

FIGS. 2 and 3 clearly show that not all the facing, adjacent peak areas 3, 3*a*, 3'*a*, 3*b* of the meander paths 2, 2*a*, 2*b* are interconnected by connecting areas 4, 4*a*, 4*b*, 4*c*, 4*d*, but between such connecting areas 4 to 4*d* of two adjacent meander paths 2, 2*a* are circumferentially provided several gaps 5, 5', 5*a*, 5*b*, 5*b'*. This leads to a high flexibility of the stent according to the invention. It is in particular achieved that when the stent 1 is bent at right angles to its longitudinal axis A the central area does not bend in in such a way that it loses its cross-sectionally, substantially circular contour and is pressed flat in the center in the action direction of the forces and perpendicular to the action direction of the forces is not widened in the center of its longitudinal extension as is the case with conventional stents, where all the facing, adjacent peak areas 3, 3*a* etc. of juxtaposed meander turns are firmly linked by connecting areas 4, 4*a* etc.

The connecting area 4, 4*a* etc. are in one piece with the remaining part of the stent, particularly the meander paths 2, 2*a* etc. and their adjacent areas 3, 3*a*.

It can be gathered from FIG. 1 that the substantially rhombic free spaces formed between the legs of the meander paths 2,2*a* etc. in the high temperature setting taper to slots in the low temperature setting and the legs of the meander paths 2, etc. are substantially parallel to one another.

FIG. 3 also shows that the circumferential thickness of the connecting areas 4, 4*a*, 4*b*, 4*c* is no greater than the thickness of the individual legs of the meander paths 2, 2*a*, etc. The areas 7, 7' or 7*a*, 7*a'* are welded areas, which in the closed position of the stent shown in FIG. 3 are interconnected by welded joints.

FIG. 4 shows a slotted plate from which the stent according to the invention can be produced. The stent is made from a nickel-titanium alloy, such as nitinol. In a flat plate the openings or slots 11, as shown in FIG. 4, are produced in that circumferentially adjacent slots are in each case displaced by approximately half their length in the axial direction A. In the central area of each slot 11 the latter is provided with a widening 12, so that the material bounding the widening 12 in the circumferential direction is reduced roughly to the width of the material left between the slots. If the portions 13 are left, they later form the connecting portions 4, 4*a*, etc., or in the areas where the portions 13 are removed, the free spaces or gaps 5, 5*a*, etc. are created.

After producing the plate in the form shown in FIG. 4 initially all the portions 13 are left. Only to the left is it indicated in FIG. 4 how subsequently, i.e. after producing the stent, as shown in FIGS. 1 and 2, the separations are formed for creating the gaps 5.

The plate shown in FIG. 4 is bent to form a cylinder, so that the two edges 14, 15 are in contact. At the welding points 7, 7' the welding joints are made and as a result initially a stent is formed in its low temperature position corresponding to FIG. 1. This is followed by a heat treatment, so as to give memory characteristics to the resulting stent, so that after raising the temperature to a predetermined ambient temperature, which is below the temperature of the human body, it can widen to its high temperature position corresponding to FIG. 2.

After producing and heat treating the stent in this way, the bridges 13 are removed in the desired manner, so that the connecting areas or webs 4, 4*a*, etc. or free spaces 5, 5', 5*a*, etc. are formed, in the manner described hereinbefore. In FIG. 3 between two circumferentially succeeding connecting areas or webs 4, 4*a* are in each case formed two free spaces 5 of adjacent, facing areas 3, 3*a* of the meander turns 2, 2*a*. The portions between the joining areas 4 in the circumferential direction can also be made larger. As a rule, there should be at least two free spaces 5 between two circumferentially succeeding webs 4.

The invention provides a highly flexible stent, which can follow all the bends without any deterioration.

We claim:

1. A stent comprising a hollow, elongated body having a longitudinal axis of symmetry, said body being formed of a material having material areas and gaps between them so that after said stent is inserted into a lumen of an organ said stent can keep the lumen open while permitting tissue to grow round the stent with said body material comprising a plurality of elongated meander paths arranged adjacent one another successively over the surface of said body, plural connecting parts extending between and connecting each two adjacent meander paths, said connecting parts being relatively short in length as compared to the width of each of the two associated elongated meander paths, and said connecting parts between each two adjacent meander paths being spaced from one another along the length of the adjacent, connected meander paths by at least two non-interconnected meanderings of each meander path.

2. The stent according to claim 1, wherein each of said meander paths includes legs connected with one another along their associated meander path by turns which form peaks of the meander path facing adjacent meander paths.

3. The stent according to claim 2, wherein said connecting parts are connected to peaks of said meander paths.

4. The stent according to claim 3, wherein peaks of adjacent meander paths are aligned with one another along the length of the elongated meander paths.

5. The stent according to claim 4, wherein said aligned peaks are oppositely directed peaks.

6. The stent according to claim 1, wherein said elongated meander paths extend over a circumference of said stent.

7. The stent according to claim 1, wherein said stent has a cross-sectionally, substantially circular contour and a high bending flexibility such that when it is bent at right angles to its longitudinal axis the stent does not lose its cross-sectionally, substantially circular contour.

8. The stent according to claim 7, wherein said hollow, elongated body is cylindrical.

9. The stent according to claim 1, wherein said hollow, elongated body is cylindrical.

10. The stent according to claim 1, wherein said body material is a memory alloy.

11. A method of keeping open a lumen of an organ comprising providing a stent having a hollow, elongated body with a longitudinal axis of symmetry and inserting said stent into said lumen of said organ to keep the lumen open, wherein said stent body is formed of a material having material areas and gaps between them so that after said stent is inserted into said lumen said stent can keep the lumen open while permitting tissue to grow round the stent with said body material comprising a plurality of elongated meander paths arranged adjacent one another successively over the surface of said body, plural connecting parts extending between and connecting each two adjacent meander paths, said connecting parts being relative short in length as compared to the width of each of the two associated elongated meander paths, and said connecting parts between each two adjacent meander paths being spaced from one another along the length of the adjacent, connected meander paths by at least two non-interconnected meanderings of each meander path whereby said stent has a relatively high bending flexibility such that when it is bent at right angles to its longitudinal axis the stent does not have its cross-sectional contour deformed.

12. The method according to claim 11, wherein said inserting includes expanding the stent when inserted into the lumen to widen the lumen.

13. The method according to claim 12, wherein said body material is a memory alloy such that said stent expands to widen said lumen after its temperature is raised to a predetermined ambient temperature, which is below the temperature of the organ.

* * * * *